US00PP36696P2

(12) United States Plant Patent
Grazzini

(10) Patent No.: US PP36,696 P2
(45) Date of Patent: May 20, 2025

(54) ***DIANTHUS* PLANT NAMED 'G22089'**

(50) Latin Name: *Dianthus hybrida*
Varietal Denomination: G22089

(71) Applicant: Garden Genetics llc, Columbus, OH (US)

(72) Inventor: Richard A. Grazzini, Columbus, OH (US)

(73) Assignee: Garden Genetics, Columbus, OH (US)

( * ) Notice: Subject to any disclaimer, the term of this patent is extended or adjusted under 35 U.S.C. 154(b) by 0 days.

(21) Appl. No.: 18/925,698

(22) Filed: Oct. 24, 2024

(51) Int. Cl.
*A01H 5/02* (2018.01)
*A01H 6/30* (2018.01)

(52) U.S. Cl.
USPC ..... Plt./278
CPC ..... *A01H 6/305* (2018.05)

(58) Field of Classification Search
USPC ..... Plt./278, 283
CPC ..... A01H 5/02
See application file for complete search history.

*Primary Examiner* — Kent L Bell
(74) *Attorney, Agent, or Firm* — Cassandra Bright

(57) ABSTRACT

A new and distinct cultivar of *Dianthus* plant named 'G22089' is disclosed, characterized by large bright red flowers with rounded, overlapping petals. Healthy glaucous blue-green foliage exhibits good field tolerance to common *Dianthus* pathogens. The new variety is a *Dianthus*, normally used for outdoor ornamental purposes.

2 Drawing Sheets

Figure 1:
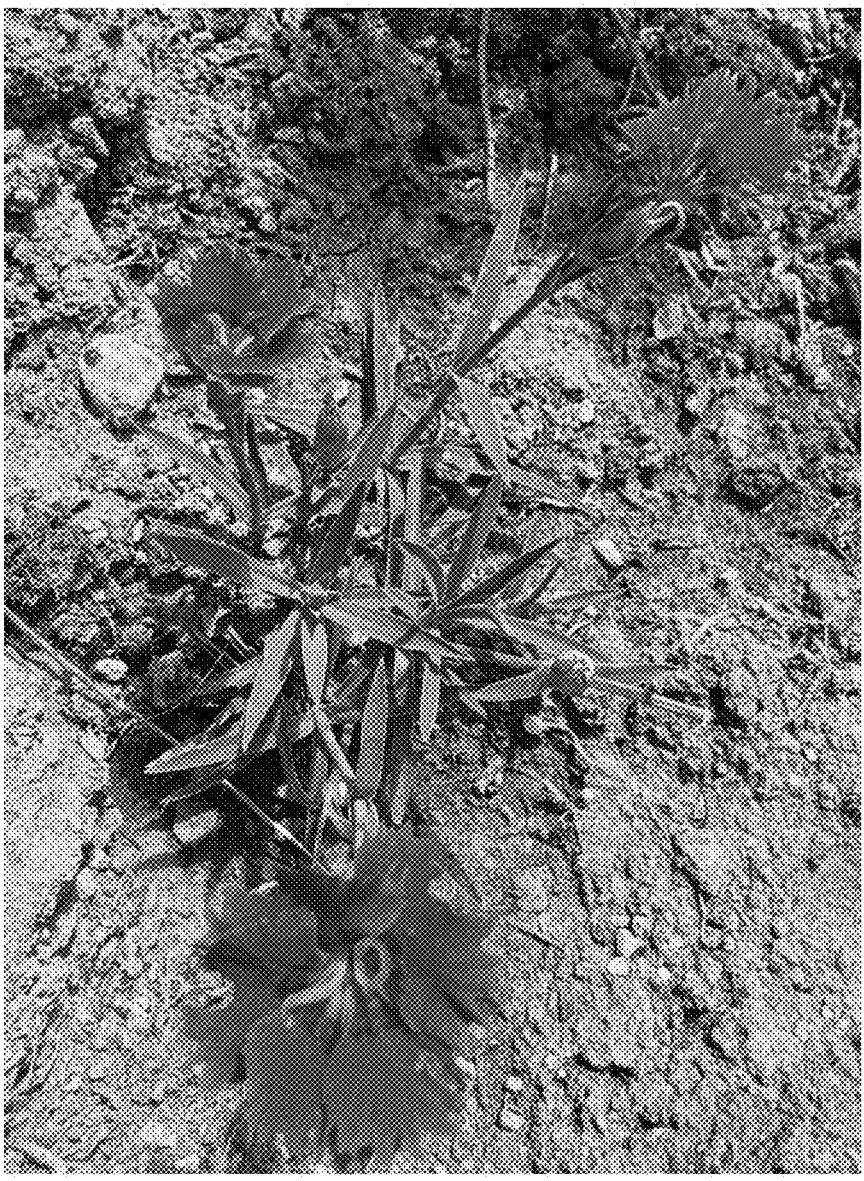

Latin name of the genus and species: *Dianthus hybrida.*
Variety denomination: 'G22089'.

BACKGROUND OF THE INVENTION

The new *Dianthus* cultivar is a product of a planned breeding program conducted by the inventor at a research nursery in Bellefonte, Pennsylvania. The cross resulting in this new variety was made in February of 2019.

The seed parent is the unpatented proprietary variety referred to as *Dianthus* 'G17-016'. The pollen parent is the unpatented proprietary variety referred to as *Dianthus* '50259-6'. The new variety was selected in November of 2019 by the inventor in a group of seedlings resulting from the 2019 cross-pollination, in a nursery in Bellefonte, Pennsylvania.

Asexual reproduction of the new cultivar was performed by vegetative cuttings. This was first performed at the same nursery in Bellefonte, Pennsylvania during January of 2020, and has shown that the unique features of this cultivar are stable and reproduced true to type in multiple successive generations.

SUMMARY OF THE INVENTION

The cultivar 'G22089' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'G22089'. These characteristics in combination distinguish 'G22089' as a new and distinct *Dianthus* cultivar:

1. Large flowers.
2. Bright red flowers with rounded, overlapping petals.
3. Spreading and dense ground-cover habit.

4. Healthy glaucous blue-green foliage.
5. Field tolerance to common *Dianthus* pathogens.
6. Strongly reblooming to constant flowering.

PARENT COMPARISONS

Plants of the new cultivar 'G22089' are similar to plants of the seed parent in most horticultural characteristics; however, plants of the new cultivar 'G22089' differ in the following:

1. Flowers of the new variety are larger than flowers of the seed parent.
2. Flower color of the new variety is bright red, while the flower color of the seed parent is pink to red.
3. Flowers of the new variety have a slight eye, while flowers of the seed parent have no eye.
4. Foliage of the new variety is glaucous blue-green, while foliage of the seed parent is mid-green.
5. Plants of the new variety do not die back in the center, while plants of the seed parent show dieback.

Plants of the new cultivar 'G22089' are similar to plants of the pollen parent in most horticultural characteristics; however, plants of the new cultivar 'G22089' differ in the following:

1. Flowers of the new variety are larger than flowers of the pollen parent.
2. Flower color of the new variety is bright red, while the flower color of the pollen parent is rose-red.
3. Flowers of the new variety have a slight eye, while flowers of the pollen parent have a larger, distinct red-violet eye.
4. Foliage of the new variety is glaucous blue-green, while foliage of the pollen parent is silver-grey.
5. Plants of the new variety do not die back in the center, while plants of the pollen parent show significant dieback.

COMMERCIAL COMPARISONS

Plants of the new cultivar 'G22089' are comparable to the commercial variety *Dianthus* 'Kahori', unpatented. The two

*Dianthus* varieties are similar in most horticultural characteristics, however, the new variety 'G22089' differs in the following:

1. Flowers of the new variety are larger than flowers of this comparator.
2. Bloom time of the new variety is extended compared to the bloom time of this comparator.
3. The new variety has healthy leaves and plant crown, while this comparator tends to develop an open crown due to plant pathogens. This comparator is also prone to develop leaf spots caused by foliar pathogens.
4. Flower color of the new variety is bright red, while the flower color of this comparator is rose-pink.
5. Plants of the new variety are somewhat wider than plants of this comparator.

Plants of the new cultivar 'G22089' are comparable to the commercial variety *Dianthus* 'Uribest52', U.S. Plant Pat. No. 28,239. The two *Dianthus* varieties are similar in most horticultural characteristics; however, the new variety 'G22089' differs in the following:

1. Flowers of the new variety are larger than flowers of this comparator.
2. Bloom time of the new variety is extended compared to the bloom time of this comparator.
3. Plants of the new variety are slightly taller than plants of this comparator.
4. Plants of the new variety are wider than plants of this comparator.
5. Foliage of the new variety is glaucous blue-green, while foliage of this comparator is dark green.

BRIEF DESCRIPTION OF THE PHOTOGRAPHS

The accompanying photograph in FIG. 1 illustrates a typical flowering plant of 'G22089' grown outdoors in Camarillo, CA at approximately 6 weeks old growing in the ground.

Figure 2:
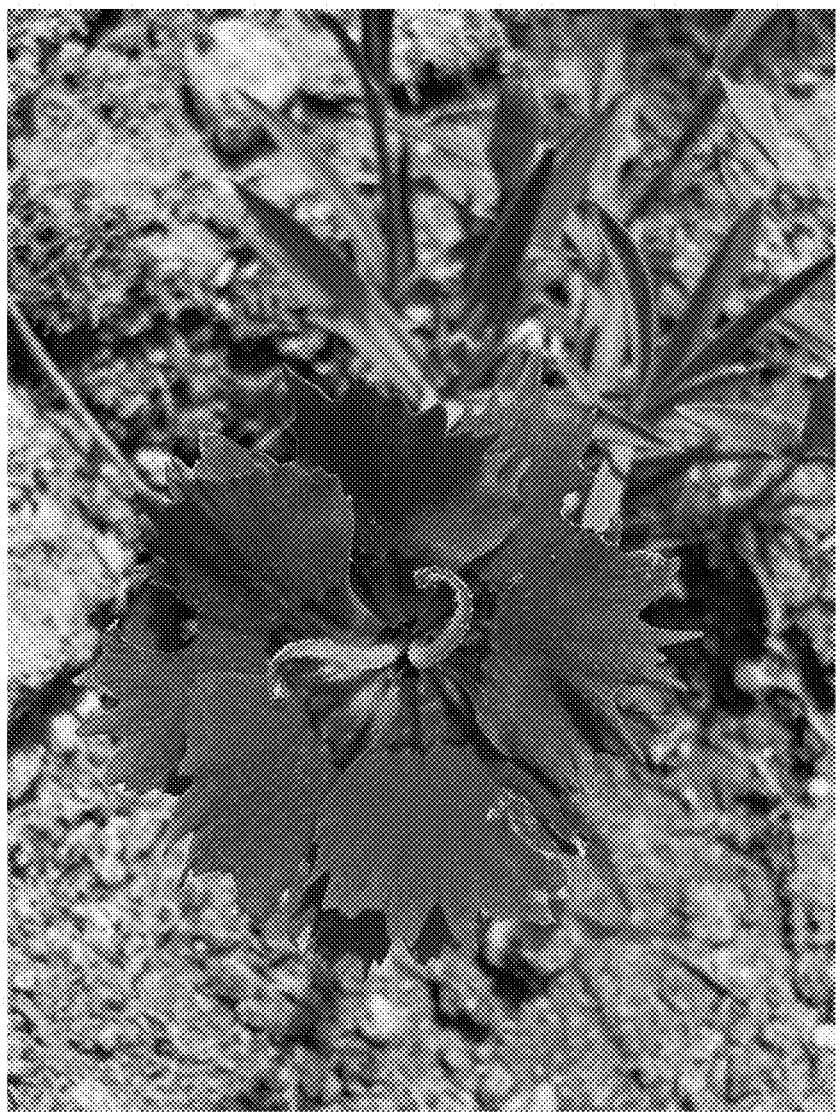

FIG. 2 illustrates a close-up view of a flower.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'G22089' plants grown outdoors in Camarillo, California. The growing temperature ranged from approximately 10° C. to 25° C. during the day and from approximately 6° C. to 12° C. during the night. General light conditions are normal sunlight and numerical values represent averages of typical plant types. Measurements were taken during June of 2021.

Botanical classification: *Dianthus hybrida* 'G22089'.

PROPAGATION

Time to initiate roots: About 10 days at approximately 24° C.

Time to produce a rooted cutting: About 18 days at 24° C.

Root description: Fibrous roots, approximately 1 to 3 mm in diameter, colored near RHS Greyed-Orange 165C.

PLANT

Age of plant described: About 10 weeks from a rooted cutting.

Container size of plant described: 1 quart.

Growth habit: Mounded flowering perennial.

Plant spread: About 20 cm.

Plant height: About 14 cm.

Plant vigor: Strong.

Length of plant stem: Average 9 to 12 cm.

Diameter of plant stem: Approximately 3 mm.

Quantity stems: 15 to 20.

Stem:

*Color*.—Near RHS Greyed-Green 189B.

*Texture*.—Smooth.

*Hollowness*.—Not observed on a plant of this age.

Internode length: 1 to 2.8 cm.

FOLIAGE

Leaf:

*Arrangement*.—Opposite (in pairs). Quantity: Approximately 4 to 8 per stem.

*Average length*.—4.5 cm.

*Average width*.—3 to 4 mm.

*Shape of blade*.—Linear.

*Apex*.—Acute.

*Base*.—Clasping.

*Attachment*.—Sessile.

*Margin*.—Entire.

*Texture of top surface*.—Smooth.

*Texture of bottom surface*.—Smooth.

*Pubescence*.—None.

*Color*.—Young foliage upper side: Near RHS Greyed-Green 189A, base 191A. Young foliage under side: Near RHS Greyed-Green 189A, with glaucous layer of 189C. Mature foliage upper side: Near RHS Green 137A with glaucous layer of 189C. Mature foliage under side: Near RHS Green 137A with glaucous layer of 189C.

*Venation*.—Type: Linear. Venation color upper side: Indistinguishable from foliage. Venation color under side: Indistinguishable from foliage.

FLOWER

Natural flowering season: Late spring into fall.

Inflorescence type and habit: Umbel of 2 to 4 flowers, 1 to 2 flowers per stem.

Flower longevity on plant: About 14 days.

Quantity of flowers: Approximately 11 to 18 flowers and buds on a 10-week-old plant.

Persistence: Persistent.

Fragrance: Moderate sweet to clove-like scent.

Inflorescence (umbel) size:

*Diameter*.—Approximately 5 to 7 cm.

*Height*.—Approximately 3 to 5 cm.

Individual flower size:

*Diameter*.—Approximately 4 cm.

*Length*.—Approximately 3.5 cm.

Petals:

*Arrangement*.—Single overlapping whorl.

*Shape*.—Spatulate, elongated base.

*Base*.—Long attenuate.
*Margin*.—Serrated.
*Apex*.—Serrate.
*Length*.—Upper section, outside of tube: 1.9 cm. Elongated base, in tube: 2.2 cm.
*Width*.—Upper section, outside of tube: 2 cm. Elongated base, in tube: 4 mm.
*Petal quantity*.—Average 8 to 10.
*Texture*.—Smooth all surfaces.
*Aspect*.—Nearly flat.
*Color*.—When opening: Upper surface: Undertone RHS Red 53A, completely covered in flush of Red-Purple N66A. Eye halo Purple N79A. Lower surface: Near RHS Red-Purple 71B. Fully opened: Upper surface: Undertone RHS Red 53B, moderately flushed Red-Purple N57A. Eye halo Purple N79B. Lower surface: Near RHS Red-Purple 59C.

Tube:
*General description*.—Tube consists of the elongated, unfused base of the petals. Tube shape caused by a fused calyx.
*Length*.—1.9 cm.
*Width*.—9 mm.
*Texture*.—Smooth.
*Color*.—Fully opened: Inner surface: Near RHS Yellow-Green 142D. Near RHS Green 138D. 2 Outer surface:

Bud:
*Shape*.—Elongated cylinder.
*Length*.—Average 1.8 cm.
*Diameter*.—Average 9 mm.
*Color*.—Appearing petals colored near RHS Red-Purple 61A.

Sepals:
*Quantity*.—5.
*Arrangement*.—Fused tube.
*Shape*.—Cylindric.
*Length*.—1.3 cm.
*Width*.—5 mm.
*Margin*.—Entire.
*Apex*.—Acute.
*Texture*.—Smooth, upper and lower surfaces.
*Color*.—Near RHS Green 138C.

Bracteoles:
*Shape*.—Deltoid.
*Quantity*.—2-5 per flower.
*Length*.—Average 3 to 6 mm.
*Width*.—Average 2 to 4 mm.
*Margin*.—Entire.
*Texture*.—Smooth.
*Color*.—Near RHS Green 138B.

Peduncle:
*Length*.—Average 4.4 cm.
*Diameter*.—3 mm.
*Color*.—Near RHS Green 138B, with glaucous layer of Green 189C.
*Orientation*.—Upright.
*Strength*.—Moderate.
*Texture*.—Smooth.

REPRODUCTIVE ORGANS

Stamens:
*Number*.—About 8 to 10.
*Filament length*.—1.9 cm.
*Filament color*.—Near RHS Red-Purple 65C.

Anthers:
*Shape*.—Linear.
*Length*.—3 mm.
*Color*.—RHS Red-Purple 59B.
*Pollen*.—Not observed.

Pistil:
*Number*.—1, 2 stigmas.
*Length*.—3.7 cm.
*Style*.—Number: 2. Length: Approximately 3.1 cm. Color: Base near RHS Red-Purple 65D, upper-section Red-Purple 59B.
*Stigma*.—Shape: Linear. Color: Near RHS Red-Purple 59A.
*Ovary*.—Shape: Oblong. Diameter: 5 mm. Length: 9 mm. Color: Near RHS Green 138D.

OTHER CHARACTERISTICS

Fruits and seeds: Not observed to date.
Disease/pest resistance: Shows good field-tolerance to common *Dianthus* pathogens. Specific pathogens resistance has not been determined.
Temperature range: Winter hardiness to at least USDA Zone 5.

What is claimed is:

1. A new and distinct cultivar of *Dianthus* plant named 'G22089' as herein illustrated and described.

* * * * *